United States Patent [19]

Philapitsch et al.

[11] Patent Number: 5,330,907
[45] Date of Patent: Jul. 19, 1994

[54] METHOD OF PREPARING ACTIVATED PROTEIN C

[75] Inventors: Anton Philapitsch, Ebenfurt; Hans P. Schwarz, Vienna, both of Austria

[73] Assignee: Immuno Aktiengesellschaft, Vienna, Austria

[21] Appl. No.: 899,869

[22] Filed: Jun. 17, 1992

[30] Foreign Application Priority Data

Jun. 20, 1991 [AT] Austria .................................. 1238/91

[51] Int. Cl.$^5$ .............................................. C12N 9/00
[52] U.S. Cl. ................................... 435/217; 435/68.1; 435/23; 530/380
[58] Field of Search ................. 530/412, 395, 407–410, 530/350, 380; 435/13, 183, 212, 214, 215, 217, 68.1, 183, 23

[56] References Cited

U.S. PATENT DOCUMENTS 4,489,403  7/1989  Stocker et al. ............................. 514/2

FOREIGN PATENT DOCUMENTS 0287028  10/1988  European Pat. Off. .
0416890   3/1991  European Pat. Off. .

OTHER PUBLICATIONS

Ehrlich et al., 1990, EMBO Journal, 9, 2367–2373, "Recombinant Protein C Derivatives . . . ".

Cho et al., 1984, Active-Site Mapping . . . , Biochemistry, 23:647.

Loscalzo, J., 1990, (Apr.), An Overview of Thrombolytic Agents, Chest 97(4):1175–1195.

Comp et al., 1982, Activation of Protein C in vivo, J. Clin. Invest., vol. 70:127–134.

G. Kohler et al., "Continuous Cultures of Fused Cells Secreting Antibody of Predefined Specificity", Nature, vol. 256, Aug. 7, 1975, pp. 495–497.

O. Taby et al., "Inhibition of Activated Protein C by Aprotinin and the Use of the Insolubilized Inhibitor for its Purification", Thrombosis Research, vol. 59, 1990, pp. 27–35.

Bajaj et al., "A Procedure For Isolation Of Human Protein C and Protein S", Preparative Biochemistry, 13(3), 191–214, 1983.

Henriksson et al., "Effect of Leukocytes, Plasmin and Thrombin on Clotting Factors", Thrombosis Research, 16:301–312, 1979.

Primary Examiner—Robert J. Hill, Jr.
Assistant Examiner—Sally P. Teng
Attorney, Agent, or Firm—Foley & Lardner

[57] ABSTRACT

To produce activated protein C, protein C is treated with plasmin. Activation is effected in a quick and simple manner. Contamination of the activated protein C with thrombin is avoided.

7 Claims, 1 Drawing Sheet

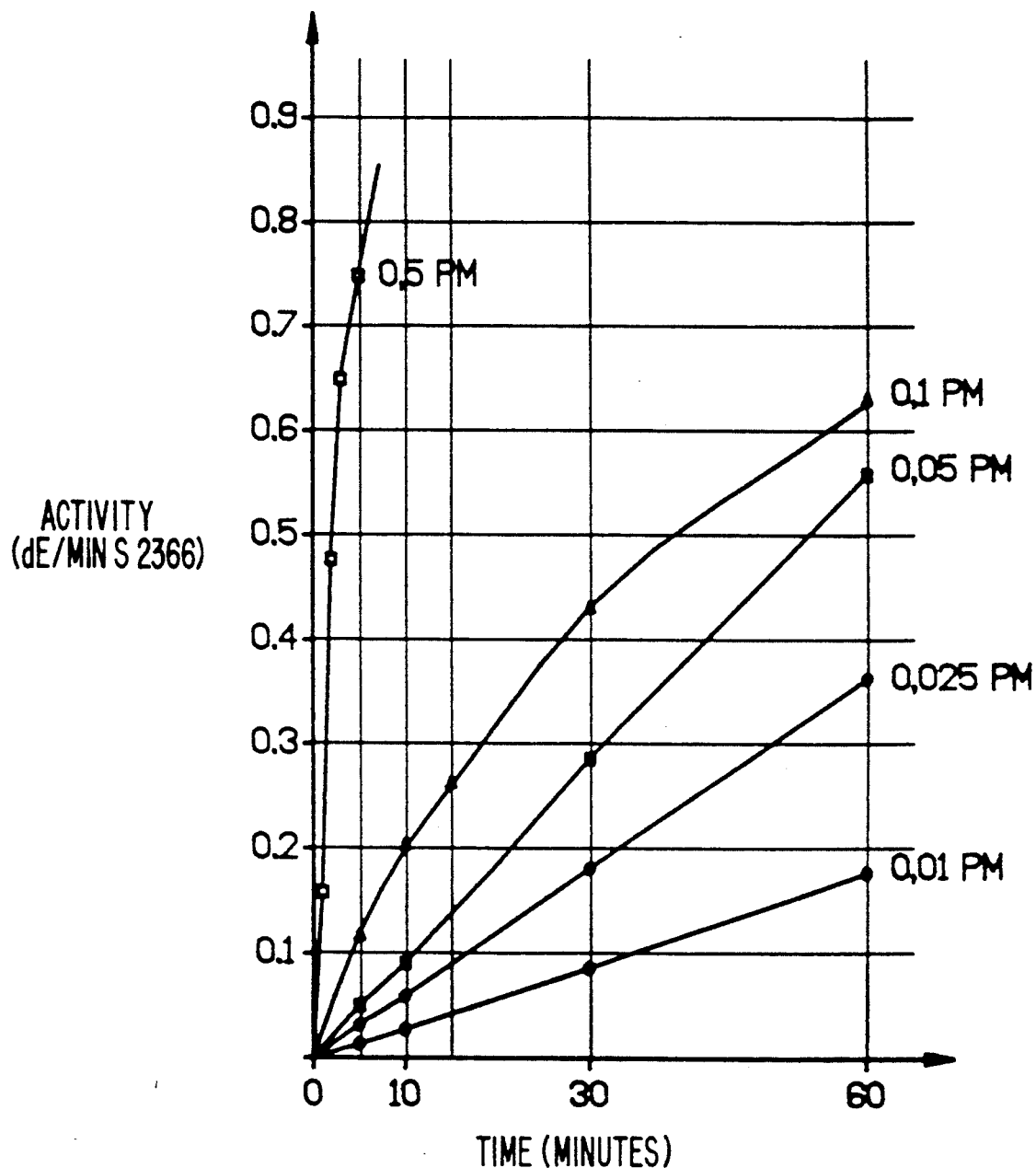

METHOD OF PREPARING ACTIVATED PROTEIN C

FIELD OF THE INVENTION

The invention relates to a method of preparing activated protein C, wherein protein C is treated with a protease.

DESCRIPTION OF THE RELATED ART

Protein C is a vitamin K-dependent glycoprotein that is synthesized in the liver and circulates in plasma as an inactive zymogen at a concentration of 4 μg/ml. It is converted into the active serine protease (activated protein C) by the thrombin-thrombomodulin complex on the surface of the vessel wall (endothelium). Protein C also may be activated by some non-physiologic enzymes, such as the snake-venom factor PROTAC ® C, available from Pentapharm Ltd. It is known that activated protein C has fibrinolytic properties due to the inactivation of plasminogen activator inhibitor and a yet unknown protein-S-dependent mechanism. It also has an anticoagulant effect, because it proteolytically degrades both factor Va, the cofactor for the factor Xa-induced prothrombin activation (thrombin formation), and factor VIIIa, the cofactor for the factor IXa-induced factor X activation.

The activation of protein C in vivo constitutes a negative feedback reaction in the generation of thrombin. In order to develop the optimum biologic activity, a cofactor (protein S) is necessary.

The activation of plasmatic protein C ex vivo is known and is carried out by treatment with activators, such as thrombin, thrombin-thrombomodulin complex or snake venom.

In EP-A-0 287 028 protein C is activated by the addition of thrombin-thrombomodulin complex. The reaction is stopped by the inhibition of thrombin with antithrombin III, whereupon the activated protein C is purified by way of affinity chromatography.

In Thrombosis Research 59, 27–35 (1990) the activation of protein C by contacting dissolved or immobilized thrombin or by recalcification of a prothrombin complex preparation is described. The thrombin used is of bovine origin, thus involving the risk of contamination of the product with bovine substances. That activation process, furthermore, has the disadvantage of the activated protein C becoming contaminated with traces of thrombin, wherefor a series of affinity chromatographic purification steps are required following upon activation.

SUMMARY OF THE INVENTION

The invention has as its object to provide an improved process for the activation of protein C that does not have the disadvantages pointed out above.

With a method of the initially defined kind, this object is achieved according to the invention by relating protein C with plasmin.

BRIEF DESCRIPTION OF THE DRAWING

The FIGURE illustrates the result of activation of protein C with plasmin at various protein C/plasmin ratios. Time (minutes) is plotted on the abscissa, and activity (dE/min S 2366) is plotted on the ordinate.

DETAILED DESCRIPTION OF THE INVENTION

It has been shown that plasmin, the key enzyme of fibrinolysis, effects the activation of protein C in a quick and simple manner such that a completely new activation process is feasible.

The activation of protein C is advantageously carried out at a protein C/plasmin ratio (μg/CU) of between 80 and 40,000, preferably of between 4,000 and 40,000. Most preferably, the activation is carried out at temperatures around 37° C. Human plasmin can readily be produced from human plasminogen or is commercially available (e.g., from Kabi).

The activation according to the invention occurs quickly, i.e., sometimes even within a few minutes, for which reason the addition of calcium ions (5 to 50 mmol/l) may be advantageous in some cases in order to decelerate the reaction.

The activation of protein C with plasmin, as opposed to thrombin, has the advantage that traces of the activator in a protein C preparation even intensify its anticoagulative and/or fibrinolytic effects.

Since plasmin as a protease is capable of further degrading activated protein C, in particular at high plasmin concentrations, it is advantageous to stop the reaction after a relatively short period of incubation by the addition of a plasmin inhibitor, such as antithrombin III or antithrombin III-heparin complex. The reaction may, for instance, be stopped as a desired degree of activation (for instance, at an activity of at least 0.15 dE/min S 2366) is reached.

A protein C activated by plasmin treatment does not differ from a protein C conventionally activated with thrombin in respect of its activity or according to SDS-PAGE analysis.

The invention will be described in more detail in the following.

EXAMPLES

Preparation of Protein C

Highly purified protein C was recovered from a crude protein C fraction obtained from commercially available prothrombin complex concentrate. Purification was effected by affinity chromatography by means of monoclonal antibodies. Monoclonal anti-protein C antibodies were produced as follows:

BALB/C mice were immunized with 100 μg human protein C by intraperitoneal injection at two-week intervals. After six weeks, another 50 μg of human protein C were injected and fusion was carried out three days later. The myeloma cell line (P3-X-63-AG8-653, $1.5 \times 10^7$ cells) was mixed with $1.7 \times 10^8$ mouse spleen cells and fused according to the modified method of Köhler & Milestein by using PEG 1500 (Köhler G., Milestein C., Nature 256 (1975), 495–497).

Positive clones, assayed by means of ELISA, were subcloned twice. Ascites production was effected by injection of $5 \times 10^6$ hybridoma cells per BALB/C mouse two weeks after Pristan treatment.

The immunoglobulin was purified from ascites by means of ammonium sulfate precipitation and subsequent chromatography on QAE-Sephadex and, further, by chromatography on Sephadex G200. To reduce the risk of transmission of murine viruses, the antibody was subjected to a further virus inactivation step prior to immobilization. The monoclonal protein C antibodies thus obtained were coupled to CNBr-Sepharose 4B (Pharmacia). The following buffers were used for the purification of protein C by means of affinity chromatography:

Adsorption buffer: 20 mM Tris, 2 mM EDTA, 0.25M NaCl and 5 mM benzamidine;
Washing buffer: 20 mM Tris, 1M NaCl, 2 mM benzamidine, 2 mM EDTA, pH 7.4;
Elution buffer: 3M NaSCN, 20 mM Tris, 1M NaCl, 0.5 mM benzamidine, 2 mM EDTA.

In detail: The prothrombin complex concentrate was dissolved in the adsorption buffer, with approximately 10 g of the prothrombin complex concentrate being employed for a 20 ml monoclonal antibody column. Subsequently, the dissolved prothrombin complex concentrate was filtered, centrifuged at 20,000 r.p.m. for 15 min and sterilely filtered through a 0.8 μm filter. The sterilely filtered and dissolved prothrombin complex concentrate was applied to the column at a flow rate of 10 ml/h. Subsequently, the column was washed free of protein with the washing buffer, and finally the bound protein C was eluted by means of the elution buffer at a flow rate of 5 ml/h and the fractions were collected. The eluted protein C was dialyzed against a buffer (0.2 mol/l Tris, 0.15M glycine and 1 mM EDTA, pH 8.3). Protein C antigen concentration was determined using the method described by Laurell, and protein C activity was determined using PROTAC activation.

The protein C eluate thus obtained was finished to a pharmaceutically applicable preparation in the following manner:

The eluate was first subjected to ultrafiltration and diafiltration steps. Diafiltration was carried out with a buffer containing 150 mmol NaCl and 15 mmol trisodium citrate.2H$_2$O per liter, at a pH of 7.4. The obtained filtrate was then freeze-dried and virus inactivated by a one-hour vapor treatment at 80° C.±5° C. and at 1375±35 mbar, carried out in accordance with the procedures defined in U.S. Pat. No. 4,640,834.

The lyophilized, virus inactivated material was then dissolved in a sterile isotonic NaCl solution and possibly present antibodies or serum amyloid P were eliminated by means of ion exchange chromatography on Q-Sepharose. The purified solution was concentrated by means of an additional ultrafiltration and diafiltration step. After this step, 10 g albumin, 150 mmol NaCl and 15 mmol trisodium citrate per liter were added to the solution obtained. The pH of the solution was 7.5. Neither murine immunoglobulin nor factors II, VII, IX and X could be detected.

Subsequently, the solution was sterilely filtered, filled in containers and lyophilized. The specific activity was 14 units protein C per mg. One unit of protein C activity is defined as the protein C activity in 1 ml normal plasma and is calibrated against the first international standard of protein C. An amidolytic assay was used as the activity test, wherein protein C was activated by means of PROTAC (Pentapharm).

Activation of Protein C with Plasmin

Protein C was dissolved in a physiologic saline solution to obtain a solution of 400 μg/ml and 10 U/ml hirudin (Sigma) were admixed. A commercially available plasmin preparation (Kabi) was dissolved in a 0.4% sodium citrate/0.7% sodium chloride buffer and diluted to five solutions having 0.01, 0.025, 0.05, 0.1 and 0.5, respectively, caseinolytic plasmin units (PM) per ml.

To activate protein C, five samples of 100 μl protein C-hirudin solution each were mixed with 100 μl of the above plasmin solutions. After 1, 5, 10, 30 and 60 minutes of incubation at 37° C., the plasmin reaction was stopped by the addition of 100 μl atheplex solution (antithrombin III-heparin complex, prepared according to EP-B-0 129 534, 23 U antithrombin III/ml and 150 U heparin/ml 0.9% NaCl solution). The activity of the activated protein C was amidolytically measured by means of a specific chromogenic substrate (S 2366, Kabi H-pyroglutamyl-L-prolyl-L-arginine-p-nitroanilide hydrochloride). The results are apparent from the annexed graph, the time in minutes being plotted on the abscissa and the activity (dE/min S 2366) being plotted on the ordinate. The graph demonstrates that the activation of protein C by means of plasmin is both time and dose-dependent. During the reaction, the ratio of protein C to plasmin (μg/CU) was 40,000:1, 16,000:1, 8,000:1, 4,000:1 and 800:1, respectively.

In addition, it has been shown that plasmin not only activates protein C, but also causes the degradation of activated protein C at an extended time of exposure. In particular, this holds true with a protein C/plasmin ratio of less than 80 μg/CU. For instance, at a protein C/plasmin ratio of 8 μg/CU an incubation for 60 minutes results in the total degradation of activated protein C.

Immunoblotting of Activated Protein C

Immunoblotting was carried out by means of protein C activated with plasmin as well as by a thrombin-activated protein C and a protein C activated with Protac (by Pentapharm). It was demonstrated that activated protein C—irrespective of the type of activation—always yields the same immunoblot.

What we claim is:

1. A method of preparing activated protein C comprising activating protein C with plasmin, wherein said activation is carried out at a protein C/plasmin ratio of between 4,000 and 40,000 μg/CU.

2. The method as claimed in claim 1, wherein said activation is carried out in the presence of Ca$^{2+}$ ions.

3. A method as set forth in claim 2, wherein said calcium ions are present in an amount of between 5 and 50 mmol/l.

4. A method as set forth in claim 1, further comprising stopping said activation by adding a plasmin inhibitor.

5. A method as set forth in claim 4, wherein said plasmin inhibitor is antithrombin III or antithrombin III-heparin complex.

6. A method as set forth in claim 1, wherein said activation is carried out at a temperature of about 37° C.

7. A method of preparing activated protein C comprising the steps of:
 (A) purifying protein C;
 (B) activating protein C by treating said purified protein C of step (A) with plasmin, wherein said activation is carried out at a protein C/plasmin ratio of between 4,000 and 40,000 μg/CU; and
 (C) stopping the reaction of said plasmin and said protein C of step (B) by addition of a plasmin inhibitor.

* * * * *